United States Patent [19]
Kennedy et al.

[11] Patent Number: 5,609,567
[45] Date of Patent: Mar. 11, 1997

[54] DISPOSABLE TRACTION SPLINT

[75] Inventors: Thomas P. Kennedy, Key Biscayne, Fla.; Howard Schiffman, New City, N.Y.

[73] Assignee: Effie Technologies,, Cocoa Beach, Fla.

[21] Appl. No.: 405,223

[22] Filed: Mar. 16, 1995

[51] Int. Cl.⁶ ...................................................... A61F 5/00
[52] U.S. Cl. .................................................................. 602/5
[58] Field of Search .......................... 602/5, 6; 128/869, 128/870, 877; 229/100, 103.3, 106, 115

[56] References Cited

U.S. PATENT DOCUMENTS

| | | | |
|---|---|---|---|
| 2,141,100 | 12/1938 | Warden | 5/82 |
| 2,384,779 | 9/1945 | Williams | 128/84 |
| 2,409,195 | 10/1946 | Crawford | 128/87 |
| 2,700,383 | 1/1955 | Moodie | 128/87 |
| 3,624,745 | 11/1971 | Bowers | 602/5 |
| 3,750,660 | 8/1973 | Muller | 602/5 |
| 4,209,011 | 6/1980 | Peck et al. | 128/87 R |
| 4,383,526 | 5/1983 | Robins | 128/87 R |
| 4,776,327 | 10/1988 | Russell | 602/5 |

*Primary Examiner*—Richard J. Apley
*Assistant Examiner*—Kim M. Lee
*Attorney, Agent, or Firm*—Walter C. Farley

[57] ABSTRACT

A disposable splint for holding a broken leg of a patient in traction is made of layered, corrugated cardboard or the like and has central, side and end panels. The panels at a proximal end are foldable to form an open end to engage the ischia of the patient. The side panels are foldable to be perpendicular to the central panel. At the distal end, a panel is foldable to form a foot plate having a central opening through which a tension strap can be passed from the patient's ankle to a tension rod. On the outer surface of the foot plate, laterally extending flaps are foldable to form supports with central slots to receive the tension rod. When applied to a patient, the leg is placed in traction manually, the splint is applied and the tension strap and rod are used to maintain the leg in traction so that the patient can be safely transported for further medical care.

4 Claims, 3 Drawing Sheets

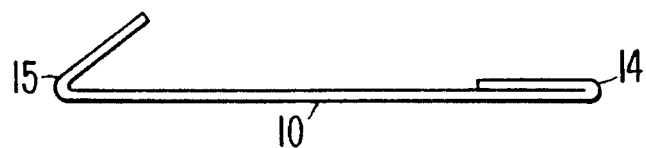
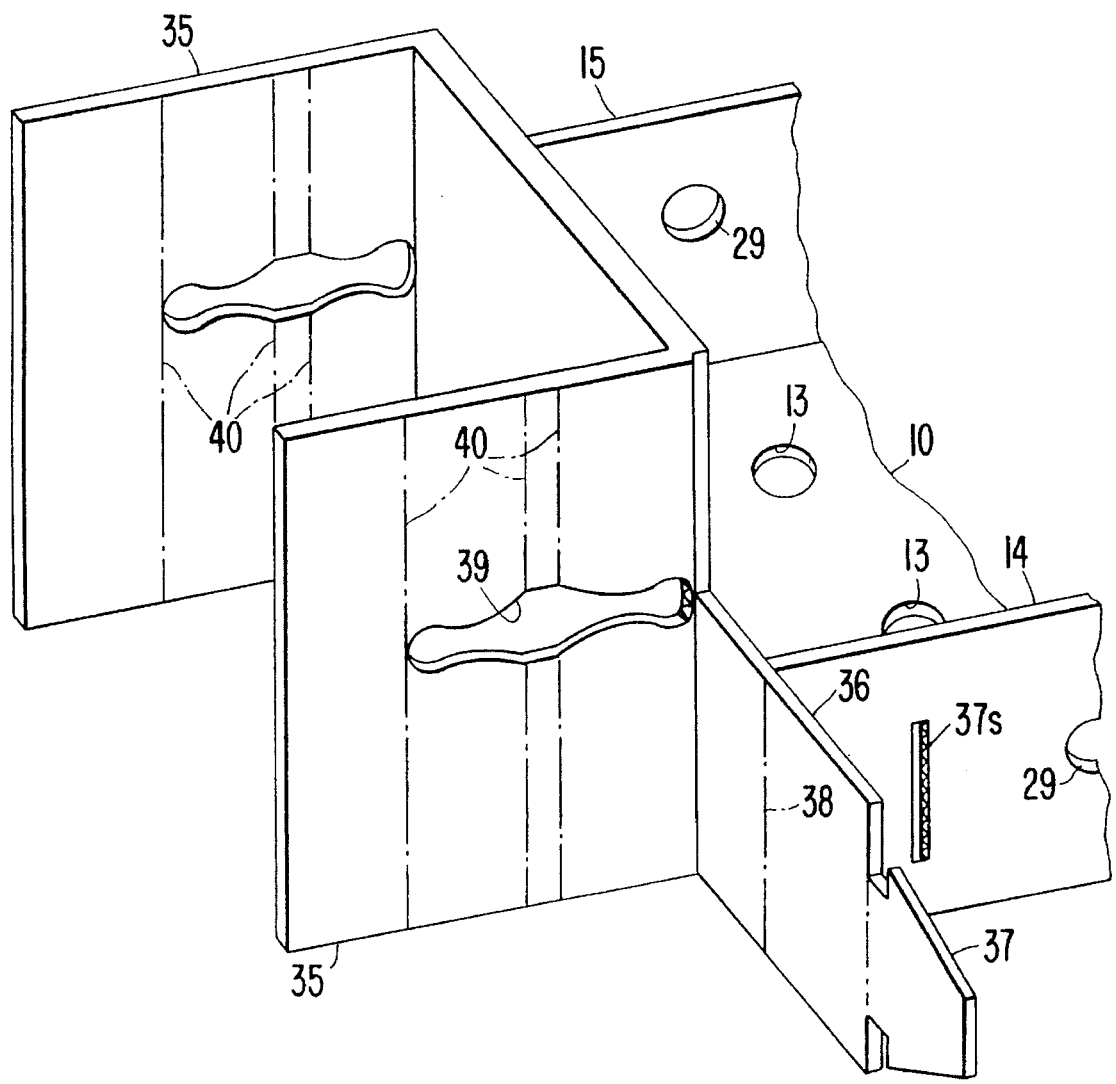

5,609,567

DISPOSABLE TRACTION SPLINT

FIELD OF THE INVENTION

This invention relates to an improved disposable traction splint which is easily applied and has greater strength than disposable splints of the prior art.

BACKGROUND OF THE INVENTION

U.S. Pat. NO. 4,383,526, which is hereby incorporated by reference, describes and claims a disposable traction splint which is the invention of Seymour Robins. While that splint is quite usable, there are some disadvantages to its structure. In a device of this type which is used almost exclusively under emergency conditions, there are several factors which are of primary importance including the speed and ease of applying the splint to a patient, the strength of the splint and the effectiveness of the splint to hold an injured limb, specifically in the present case, a fractured femur.

BRIEF SUMMARY OF THE INVENTION

An object of the present invention is to provide a traction splint in which the ease and speed of applying the splint are improved and the strength of the applied splint is greater than the prior art.

Briefly described, the invention comprises a temporary traction splint formed from a sheet of material such as corrugated cardboard. The splint has a central panel with parallel side fold lines along opposite side edges thereof and parallel distal and proximal end fold lines along opposite end edges. First and second side panels are joined to the central panel at the side fold lines, each side panel including first and second layers of material adhered together. The side panels are foldable along the side fold lines to positions perpendicular to the central panel, thereby forming a U-shaped receiver for an injured leg. Each side panel has a fold line at a proximal end thereof. A first extension panel is joined to the proximal end of the central panel at the proximal end fold line, and second and third extension panels are joined to the side panels at the end fold lines, the first, second and third extension panels being foldable against their respectively joined panels. Each extension panel has latching means for holding it in its folded position. A foot plate is joined to the distal end of the central panel at the distal end fold line, the foot plate comprising a central portion including two layers of material adhered together, the foot plate being foldable to a position perpendicular to the central panel and the side panels. First and second flaps extend laterally from the central portion and having means for latching the flaps in the folded position. Third and fourth flaps extend laterally from the central portion, each of the third and fourth flaps having fold lines to permit folding to form a polygonal support, each support having means defining a slot for receiving a tension rod, whereby a limb of a patient can be held in traction between the proximal end of the splint and the tension rod

BRIEF DESCRIPTION OF THE DRAWINGS

In order to impart full understanding of the manner in which these and other objects are attained in accordance with the invention, a particularly advantageous embodiment thereof will be described with reference to the following drawings, which form a part of this disclosure, and wherein:

FIG. 2 is a side elevation in section along line 2—2 of FIG. 1 showing pre-folded and glued portions of the splint;

FIG. 4 is a partial perspective view of the distal or foot end of the splint in a partially assembled condition.

DESCRIPTION OF THE PREFERRED EMBODIMENT

The splint of the present invention is preferably made from conventional corrugated cardboard having a corrugated inner layer and outer, flat facing layers so that it is disposable. As initially manufactured, the blank for the splint is made from a single sheet of corrugated cardboard with various cutouts. In its ready-to-use condition as manufactured and sold, the splint has flat, unfolded portions and also has linear regions, referred to herein as "fold lines" which are prepared for folding by having been scored, softened or creased by pressing in a manner well known in the cardboard processing field and which are illustrated in the various figures as dashed lines. In addition, there are certain portions which are pre-folded and held together by adhesive to form double-thickness areas for additional strength, as well as to facilitate erection for use.

Figure 1:
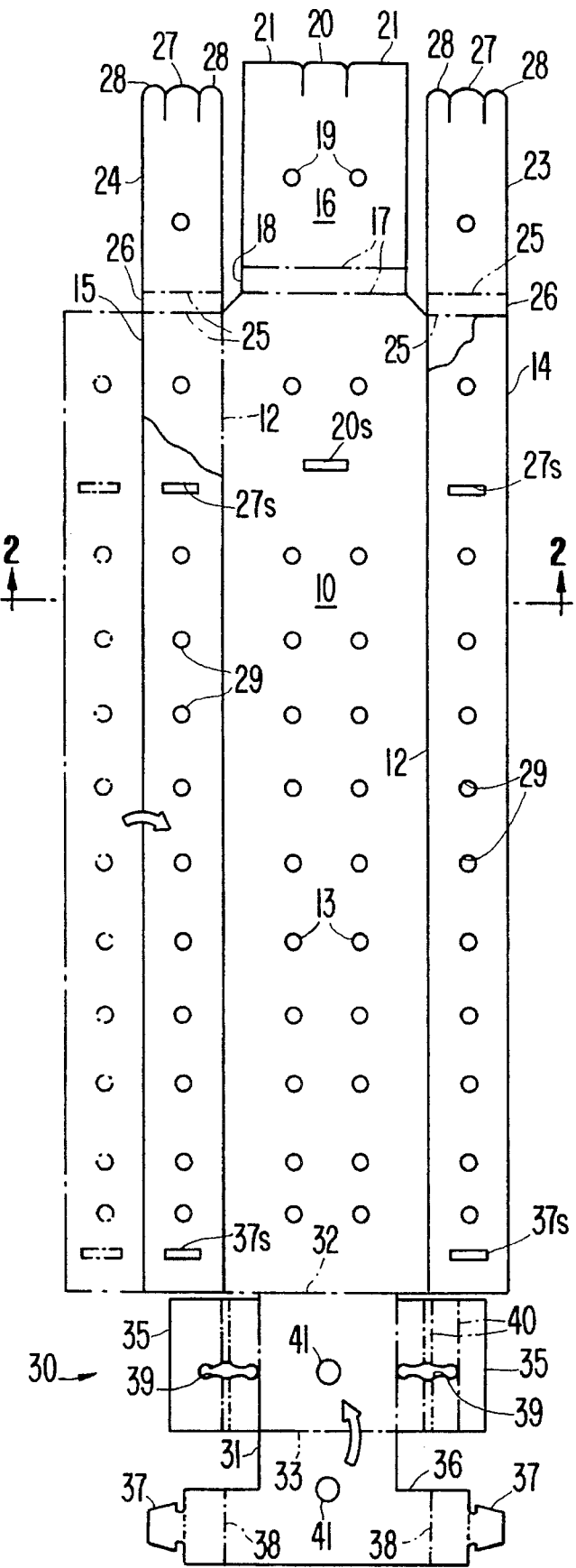
FIG. 1 is a top plan view of a splint in accordance with the invention in its fully open condition before erection and assembly.

As shown in FIG. 1, the splint comprises a rectangular central panel 10 having parallel side edges which are defined by fold lines 12. Side panels 14 and 15 are attached to opposite sides of panel 10 at fold lines 12 and are also rectangular with parallel side edges. Each panel 14, 15 is made by forming a panel of twice the width of the desired finished panel, as shown in phantom lines at panel 15, and then folding that panel in half and gluing the halves together so as to form panels of double thickness as shown in FIG. 2. Panel 10 is provided with a plurality of pairs of circular openings, the centers of the openings of each pair being typically about 3 inches apart and each opening being about 0.75 inches in diameter. The pairs are typically spaced about 3 inches apart and are provided to permit passage of holding or restraining straps through the splint at various locations, depending upon the location and nature of the patient's injury and the physical size of the patient.

Figure 3:
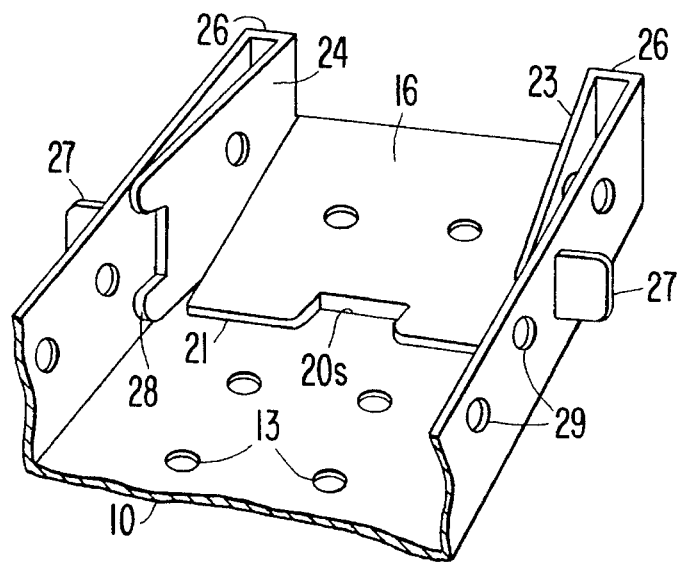
FIG. 3 is a partial perspective view of the proximal end of the splint of FIGS. 1 and 2 in an assembled and erect position.

At one end of panel 10 is an extension panel 16 which is joined to panel 10 by double parallel fold lines 17, permitting panel 16 to be folded over the adjacent end of panel 10 with an intervening narrow strip 18 between panels 10 and 16. The distal end of panel 16 has two parallel cuts to separate the end into a central tongue 20 and two outer shoulders 21. Strip 18 provides a wider surface than the edge of the cardboard to be adjacent the patient. This end of the splint will be referred to as the proximal end of the splint. Central panel 10 is provided with a slot 20s to receive tongue 20. As shown in FIG. 3, when extension 16, 17 is folded over and tongue 2b is passed through slot 20s, shoulders 21 remain on the surface of panel 10 which is visible in FIG. 1. Extension 16 has a pair of openings 19 which are alignable with the end pair of openings 13 in panel 10 when extension 16 is folded as described.

Panels 14 and 15 also have extensions 23 and 24, respectively, which are joined to panels 14 and 15 by double fold lines 25 so that strips 26 are between the respective ones of panels 14, 15 and 23, 24, in a manner similar to strip 17 and extension 16. Each of extensions 23 and 24 is provided with slits defining a central tongue 27 and outer shoulders 28. Each panel 14, 15 has a slot 27s positioned so that when extensions 23 and 24 are folded over, tongues 27 pass through slots 27s, leaving shoulders 28 against the near surface. Panels 14 and 15 are provided with openings 29 through the double thickness thereof for the passage of restraining and positioning straps. FIG. 3 shows the proximal end of the splint assembled and erected, with extensions 16, 23 and 24 folded over as described, with the respective tongues inserted in the slots provided for them, and with side panels 14 and 15 folded up so that they are perpendicular to panel 10.

At the other end of the splint, which will be referred to as the distal or foot end, is a foot plate extension indicated generally at 30, which is folded and partially glued together so that the central part is double thickness but lateral portions are not glued together and have fold lines so that they are capable of being folded in opposite directions.

More specifically, as shown in FIG. 1, the blank of foot plate 30 at the distal end includes a central foot extension 31 which is narrower than panel 10 and which is attached to panel 10 at fold line 32. Extension 31 is divided into two portions by a fold line 33, the portion attached to panel 10 having laterally extending flaps 35 and the outermost portion having laterally extending flaps 36. The distal ends of flaps 36 are provided with arrowhead-shaped tabs 37 which will be received by slots 37s in side panels 14 and 15. Fold lines 38 allow flaps 36 to be folded around the sides of panels 14 and 15. Flaps 35 have laterally extending openings 39 shaped to receive a tension rod, to be discussed later, and fold lines 40 to permit the flaps to be folded inwardly upon themselves.

In the finished product, (as sold but not erected) extension 31 is folded in upon itself along fold line 33 and glued together so that the central part of the foot plate is a substantially rigid, double-thickness body. Flaps 35 and 36 remain unglued and can be folded in opposite directions.

Figure 5:
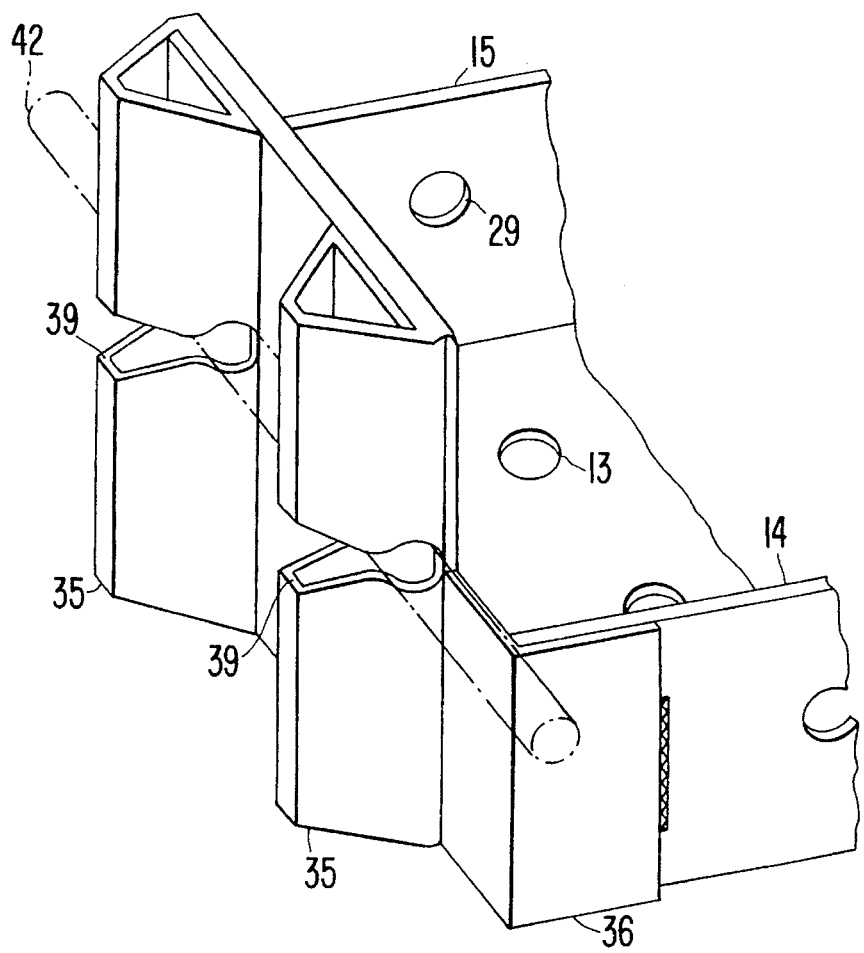
FIG. 5 is a view similar to FIG. 4 with the cardboard portion of the splint in assembled condition.

The final assembly and erection of the foot end of the splint is best understood with reference to FIGS. 4 and 5. In FIG. 4, the foot end is partially erected: sides 14 and 15 are folded up so as to be generally perpendicular with panel 10 and the end plate comprising extension portions 32 and 33 glued together has also been bent up so as to be perpendicular to panel 10 as well as to sides 14 and 15. As mentioned above, flaps 36 have fold lines 38 which allow the flaps to be folded around side panels 14, 15 whereupon arrowhead-shaped tabs 37 are inserted through slots 37s from outside to inside of the side panels as shown in FIG. 5. To do this, the ends of flaps 36 are folded toward the proximal end of the splint.

Flaps 35, however, are folded in the opposite direction and are folded upon themselves to form triangular structures with the outer surface of extension 31. In each of these triangular structures, openings 39 present a slot leading to a circular opening so that a rod 42, shown in phantom lines so as not to obscure the splint structure, can be inserted, the rod extending transversely, parallel with panel 10.

This completes the erection and assembly of the splint itself.

The use of the splint is similar in many respects to the splint shown in U.S. Pat. No. 4,383,526. When a patient having a fracture requiring the use of a traction splint is approached, the splint is removed from its package and opened up so that is appears as shown in FIG. 1, except that the foot plate is folded and glued. It is placed along side the patient with the foot end next to the patient's foot. The splint is then erected by folding up sides 14 and 15, and folding extensions 16, 23 and 24 as described above so that the central tabs in each extension pass through the slots provided for them as shown in FIG. 3. The foot end is then erected by folding flaps 36 and engaging slots 37s with tabs 37 as shown in FIGS. 4 and 5. Flaps 35 can also be bent along fold lines 40.

Along with the splint are provided several straps or bands, typically made of cotton cloth webbing, an ankle hitch with traction straps securely attached to it and a tension rod 42. The ankle hitch is a relatively wide strap with hook and loop fasteners of the type sold as Velcro®. Traction is manually applied to the fractured limb by one emergency medical technician (EMT) while the splint is being erected by another EMT. A strap is inserted through the holes in extensions 16, 23 and 24 and the holes in panels 10, 14 and 15 aligned with the extension holes. This strap is known as the ischia strap and is always used. Two or three other straps are also passed through other side and bottom holes at locations depending on the length of the patient's leg and the location of the break.

With traction still being manually applied by one EMT, the second EMT slides the splint up the leg so that the foot moves toward the foot plate. When the proximal end of the splint is adjacent the patient's crotch, the ischia strap is secured. Additional padding can be used in the crotch area. The ankle hitch is then placed around the ankle and secured and the straps attached to the ankle hitch are knotted at the sole of the patient's foot. The straps are then passed through openings 41 in the foot plate and knotted together outside of the splint. Those straps are then again knotted together around the tension rod.

At this time, the rod is turned to twist and shorten the straps attached to the ankle strap, in a manner similar to a windlass, tensioning and applying traction force to the leg, assuming the traction force previously applied by one EMT. Flaps 35 are then folded inwardly to the positions shown in FIG. 5 and rod 41 is slipped into slots 39 to the position shown in FIG. 5. The splint has now taken over the task of applying traction to the limb of the patient and the patient can be safely transported for further medical care.

It will be observed that the process of erecting the splint is a very simple one, requiring only the folding up of two side panels, folding in of three proximal end extension panels with insertion of the central tabs to secure those extensions, and folding up of the foot plate which is secured by tabs 37 inserted into the side panels. After application of the splint to the patient, the tension rod is secured by folding of flaps 35. The splint is considerably stronger and more rigid because of the doubling and gluing of the side panels and end plate, which also simplify erection of the splint. Additionally, the structure involving flaps 35 provides a simple and very secure retainer for the tension rod to reliably maintain tension on the broken limb during transportation.

While one advantageous embodiment has been chosen to illustrate the invention, it will be understood by those skilled in the art that various modifications can be made therein without departing from the scope of the invention as defined in the appended claims.

What is claimed is:

1. A temporary traction splint formed from a sheet of material comprising:

a central panel having parallel side fold lines along opposite side edges thereof and parallel distal and proximal end fold lines along opposite end edges thereof;

first and second side panels joined to said central panel at said side fold lines, each said side panel including first and second layers of material glued together, said side panels being foldable along said side fold lines to positions perpendicular to said central panel, thereby forming a U-shaped receiver, each said side panel having a fold line at a proximal end thereof;

a first extension panel joined to said proximal end of said central panel at said proximal end fold line;

second and third extension panels joined to said side panels at said end fold lines, said first, second and third extension panels being foldable against their respectively joined panels, each said extension panel having latching means for holding said extension panel in its folded position; and a foot plate joined to a distal end of said central panel at said distal end fold line, said foot plate comprising a central portion including two layers of material glued together and being foldable to a position perpendicular to said central panel and said side panels, first and second flaps extending laterally from said central portion and having means for latching said flaps in said folded position, and third and fourth flaps extending laterally from said central portion, each of said third and fourth flaps having a plurality of fold lines to permit folding said third and fourth flaps toward each other to form triangular polygonal supports, each said polygonal support having a base portion resting against said end plate and having means defining a slot for receiving an end of a tension rod, whereby a limb of a patient can be held in traction between said proximal end of said splint and a portion of said tension rod between said polygonal supports.

2. A splint according to claim 1 wherein said foot plate comprises a central opening to permit passage of a tension member from the ankle of a patient to said tension rod.

3. A splint according to claim 1 wherein each said latching means includes a tab and a slot to receive said tab.

4. A temporary traction splint formed from a sheet of material comprising:

a central panel having side fold lines along opposite side edges thereof and distal and proximal end fold lines along distal and proximal end edges thereof;

first and second side panels joined to said central panel at said side fold lines, each said side panel including first and second layers of material glued together, said side panels being foldable along said side fold lines to positions perpendicular to said central panel, thereby forming a U-shaped receiver, each said side panel having a fold line at said proximal end thereof; and a foot plate joined to a distal end of said central panel at said distal end fold line, said foot plate comprising a central portion including two layers of material glued together and being foldable to a position perpendicular to said central panel and said side panels, first and second flaps extending laterally from said central portion and having means for latching said flaps in said folded position, and third and fourth flaps extending laterally from said central portion, each of said third and fourth flaps having a plurality of fold lines to permit folding said third and fourth flaps toward each other to form triangular polygonal supports, each said polygonal support having a base portion resting against said end plate and having an apex pointing away from said proximal end of said U-shaped receiver, each said apex having means defining a slot for receiving an end of a tension rod, whereby a limb of a patient can be held in traction between said proximal end of said splint and a portion of said tension rod between said polygonal supports.

\* \* \* \* \*